United States Patent [19]

Sutter et al.

[11] 4,388,921
[45] Jun. 21, 1983

[54] DEVICE COMPRISING A PLATE AND SCREWS FOR FASTENING A PLATE TO A BONE

[75] Inventors: Franz Sutter, Niederdorf; Fritz Straumann, Waldenburg, both of Switzerland

[73] Assignee: Institut Straumann AG, Waldenburg, Switzerland

[21] Appl. No.: 266,351

[22] Filed: May 22, 1981

[30] Foreign Application Priority Data

May 28, 1980 [CH] Switzerland .................. 4156/80

[51] Int. Cl.³ .................................................. A61F 5/04
[52] U.S. Cl. .................................... 128/92 B; 3/1.9; 128/92 C; 411/537
[58] Field of Search ............ 128/92 B, 92 BA, 92 BB, 128/92 C, 92 D, 92 EB; 403/409, 407, 396, 374, 367, DIG. 8, 314, 343; 411/536, 537-538, 368

[56] References Cited

U.S. PATENT DOCUMENTS

| | | | |
|---|---|---|---|
| 2,403,541 | 7/1946 | Molat | 411/368 X |
| 3,122,048 | 2/1964 | Warner | 411/537 X |
| 3,171,518 | 3/1965 | Bergmann | 411/537 X |
| 3,552,389 | 1/1971 | Allgower et al. | 128/92 D |
| 3,596,656 | 8/1971 | Kaute | 128/92 D |
| 4,013,071 | 3/1977 | Rosenberg | 128/92 B |

FOREIGN PATENT DOCUMENTS

| | | | |
|---|---|---|---|
| 1949923 | 4/1971 | Fed. Rep. of Germany | 128/92 B |
| 2254298 | 8/1975 | France | 128/92 B |

Primary Examiner—Richard J. Apley
Assistant Examiner—David J. Isabella
Attorney, Agent, or Firm—Michael J. Striker

[57] ABSTRACT

A plate bearing against a bone has a number of clearance holes with sleeves. Openings provided in the sleeves include each a section diverging away from the bone and bounded by a conical surface. The sleeves are subdivided into tongues by means of slots cut into the free face of the collar. A screw is screwed into the bone at every clearance hole, the head of the screw being bounded by a conical or convex surface. By tightening the screw the tongues are forced apart by the head of the screw, thus clamping the sleeve in relation to the plate. This provides a guarantee, that the plate will stay rigidly connected with the screws, even if a reabsorption of bone takes place. Some of the sleeves comprise clamping parts excentric in relation to the screw axes, enabling the surgeon to press the bone pieces against each other.

15 Claims, 15 Drawing Figures

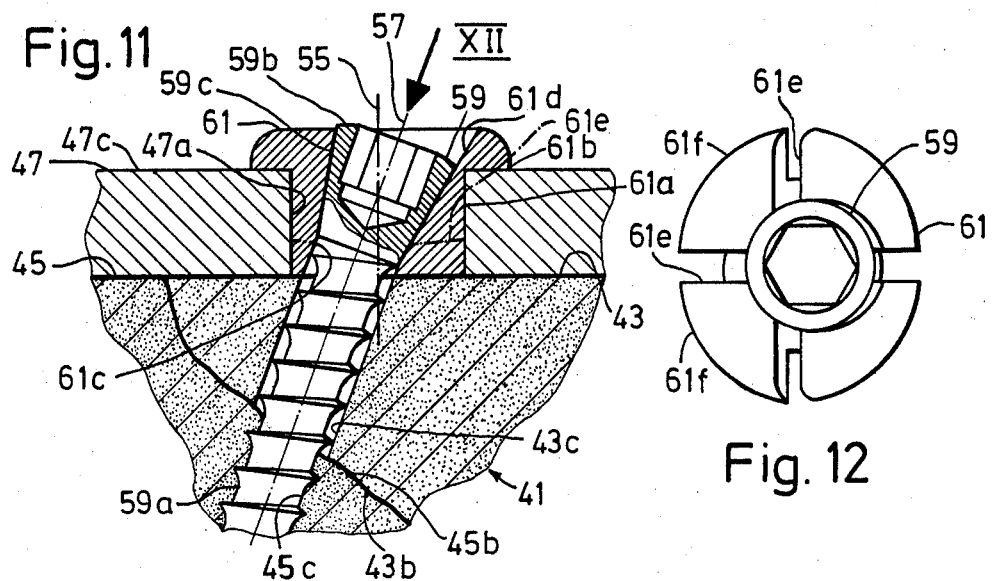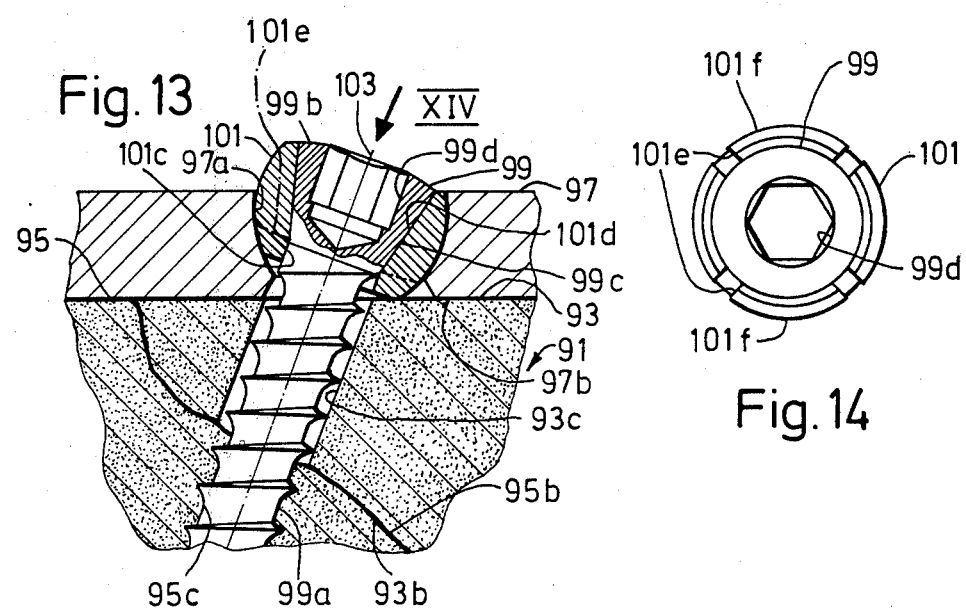

DEVICE COMPRISING A PLATE AND SCREWS FOR FASTENING A PLATE TO A BONE

BACKGROUND OF THE INVENTION

1. Field of the Invention

The invention refers to a device comprising a plate with at least two clearance holes for screws, and screws for fastening said plate to a bone, each screw including a threaded portion to be screwed into the bone and retaining means for retaining the plate.

2. Description of the Prior Art

Devices for immobilizing bone pieces and comprising plates to be screwed into the pieces of broken bone with screws have been in use in bone surgery for a long time. Attention is called in this connection to U.S. Pat. Nos. 3,552,389 and 4,219,015. The screws of this known device comprise a threaded portion and screw heads having approximately hemispherical bearing surfaces. The plates are provided with slots serving as clearance holes for the screws. Certain ones of the slots may comprise countersunk portions for receiving the screw heads and designed so, that when tightening the respective screw the plate becomes displaced in a particular direction.

If in the course of a surgical operation two pieces of bone are required to be connected with each other, it is customary to bend a plate to the proper shape and fasten it to the bone pieces, so that pressure contact is achieved between the contact surfaces. Experience has shown, however, that frictional corrosion may occur in those places in which the screws engage the plate. This happens in particular if time variable loads acting on the bone or the bone pieces are large enough to cause sections of the plate to perform micromovements, i.e. small movements, in relation to the screws and the bone pieces, in spite of the static compression force generated by the tightening process. These micromovements can also cause a reabsorption of bone material at the bearing surface of the plate. This reabsorption may cause open gaps to form between the plate and the bone pieces. The plate may then move back and forth between the screw head and the bone pieces. This may cause, under certain circumstances, a loosening of the threaded portions of the screw screwed into the bone pieces. The connection between the plate and the bone pieces continues to loosen more and more, so that the plate stops fulfilling its function of connecting the bone pieces with each other.

Mention is made here of the fact, that many different screw locking devices are known in the art. The Swiss Pat. No. 106 842, for example, discloses a screw locking device having a purpose not described in detail, but not intended for fastening implants. The screw includes a slot having a wedge inserted into it. A wood screw is disclosed, among other things, provided with a conical screw head and a slot passing through one portion of the screw shaft. A metal wedge is driven into the slot and into the material of the screwfastened portion surrounding the slot. This wedge is formed by a small plate essentially plane and provided at its forward edge with a wedge-shaped knife edge.

The Swiss Pat. No. 106 842 gives no indication to the effect, that the screw locking devices disclosed therein are intended to be used for fastening implants. The screw locking device, which comprises a wedge protruding sideways beyond the screw as disclosed in the Swiss Pat. No. 106 842 would in fact be unsuited for fastening implants, because the wedge would have to be driven into the bone plate and possibly into the bone too. However, the wedge could only be driven into the bone plate, made for example of steel, if the plate had been initially provided with slots for receiving the wedge. However, slots of this kind would cause a considerable weakening of the plate and, in addition, it would allow applying the wedge in certain definite positions of rotation of the screw only.

The Swiss Pat. No. 569 202 also discloses a screw locking device comprising a screw with a head and a threaded portion, the latter being provided with slots at its end. The screw possesses a longitudinal opening with a conical portion located in the region of the slots and a threaded portion extending in continuation of the conical portion. An expander having a conical head, a thread and a thinner shaft is screwed into the longitudinal opening. The Swiss Pat. No. 569 202 too, fails to give any indication relative to the possibility of using the screw locking device disclosed therein for surgical purposes. Since the screw locking device disclosed in Swiss Pat. No. 569 202 is subject to expansion at the free end of the threaded portion of the screw, this device too, would offer no improvement in the connection between the screw and the bone plate.

The French Offenlegungsschrift No. 2 193 161 refers to the riveting and screw-fastening of sheet metal plates. A bushing provided with a conical inner surface is first inserted in each of the bores of the plates to be connected with each other. In one illustrated embodiment, a screw having a conical neck is then inserted in a manner to produce locking, subsequent to tightening the screw. Mention is made in this connection of the fact, that the bushing could be provided with a slot extending over its entire length. The French Offenlegungsschrift thus refers to the screw-fastening of sheet metal plates and does not contain anything that would indicate that the connection disclosed therein could be adapted to the fastening of bone plates.

SUMMARY OF THE INVENTION

Thus it is a primary object of the invention, to create a plate with screws, said plate to remain stably and rigidly connected with the bone pieces or the bone even if micromovements of the type previously mentioned arise, without any frictional corrosion being meant to take place.

The foregoing and other objects are attained in accordance with one aspect of the present invention by having each screw comprise at its end adjacent to the retaining means a clamping part provided with slots and displaceable in relation to the expander in the longitudinal direction of the screw axis, the said two parts including contact surfaces in contact with one another and coaxial with the screw axis in at least one position of the screw, in which position at least one of the said two surfaces converges in the direction of the screw axis in such a manner, that by displacing the expander the clamping part may become clamped tight within the clearance hole.

Advantageous embodiments of this device may include one or more of the following features:

The diameter of each of the converging surfaces of the two parts is to preferably decrease toward the end of the screw facing away from the retaining means.

The expander is preferably made in one piece with the threaded portion of the screw and possesses, at least in part, a larger diameter than the threaded portion, said clamping part being made in the form of a separate sleeve or of a section of a separate sleeve.

The clamping part preferably comprises a section having a cylindrical outer surface, disregarding the slots, and the clearance hole is cylindrical at least in the area in clamping contact with the clamping part, the said sleeve which forms the clamping part comprising a collar made in one piece with the clamping part and protruding beyond the outer surface thereof, the collar bearing against the side of the plate which faces away from the bone. The screw axis is tilted or tiltable in relation to the axis of the outer surface of the clamping part.

The clamping part may also comprise an outer surface section which, disregarding the slots, is made in the form of a spherical surface, the clearance hole being bounded, at least in part, by a surface which is part of a spherical surface.

At least one of the clamping parts may comprise an outer surface which bears, at least in part, against the surface bounding the clearance hole and disposed excentrically in relation to the screw axis. The slots of a clamping part of this kind provided with an excentric outer surface may extend to the end surface of the clamping part which faces away from the threaded portion of the screw.

In the said one position of the screw at least one section each of the two contact surfaces of the expander and the clamping part converges in the same direction along the screw axis. At least one of the two contact surfaces of the clamping part and the expander is preferably a conical surface.

BRIEF DESCRIPTION OF THE DRAWINGS

Various objects, features and attendant advantages of the present invention will be more fully appreciated as the same becomes better understood from the following detailed description of the invention when considered in connection with the accompanying drawings, in which

FIG. 11 shows a cutout portion of FIG. 10 at a larger scale;

FIG. 12 shows a top view of a sleeve with screw looked at in the viewing direction indicated in FIG. 11 by the arrow XII;

FIG. 13 shows a sectional view corresponding to FIG. 11 of another embodiment of the device;

FIG. 14 shows a top view of a sleeve and a screw looked at in the viewing direction indicated in FIG. 13 by the arrow XIV.

DETAILED DESCRIPTION OF THE PREFERRED EMBODIMENTS

Figure 1:
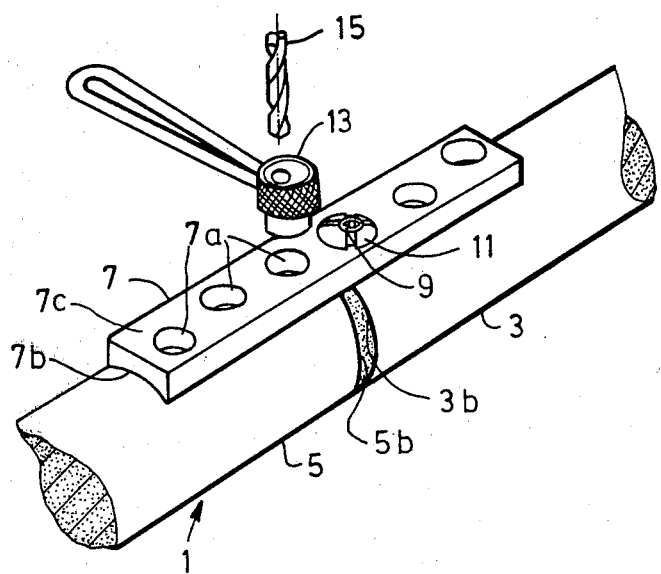
FIG. 1 shows an axonometric view with two bone pieces to be connected, a device for connecting the bone pieces comprising a partially fastened plate and drilling tools.
Figure 2:
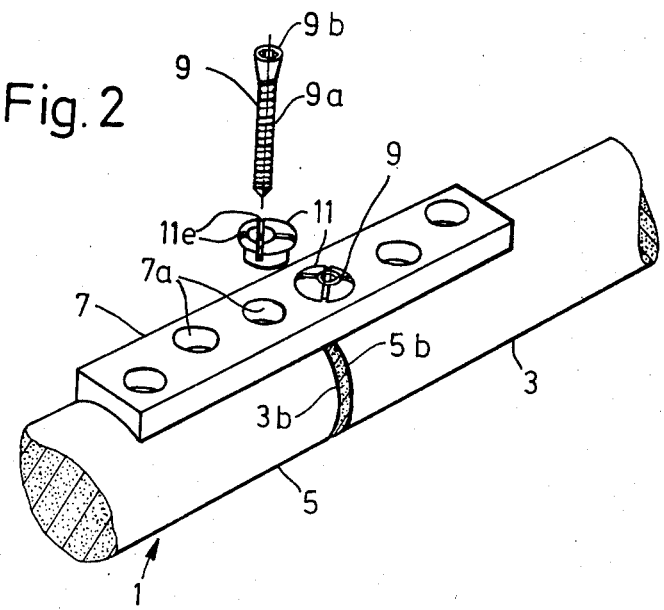
FIG. 2 shows an axonometric view of the bone pieces and the plate shown in FIG. 1 during a later phase of the surgical operation.
Figure 3:
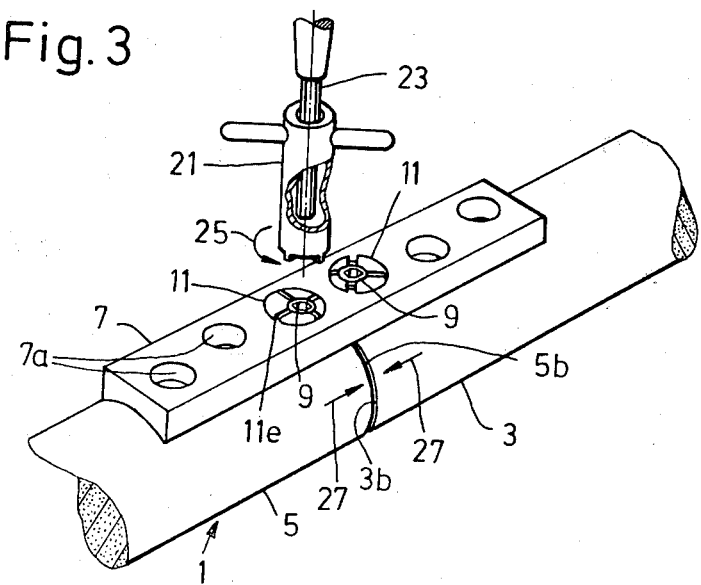
FIG. 3 shows a view of the components shown in FIG. 2 with two additional screws screwed in place, and with tools for tightening the screws and pressing the bone pieces toward each other.

FIGS. 1 to 4 show two pieces of a bone, which could be, for example, a fractured thighbone or some other broken bone. The two bone pieces 3 and 5 comprise the surfaces of fracture 3b and 5b facing toward one another. The device for connecting the two bone pieces includes a plate 7 with six cylindrical clearance holes 7a distributed over its length and bearing against the bone pieces by way of a bearing surface 7b bent to fit the shape of the bone. The surface 7c of the plate 7 which faces away from the bearing surface 7b is a plane surface, but could be bent, if required, the same way as the bearing surface. During an operation the bone pieces are laid open as much as required, and then positioned in such a way, that the surfaces of fracture bear against one another as much as possible. However, FIG. 1 is made to show the two bone pieces as separated by a relatively large open gap, to more clearly illustrate the fastening process to be described below.

Figure 5:
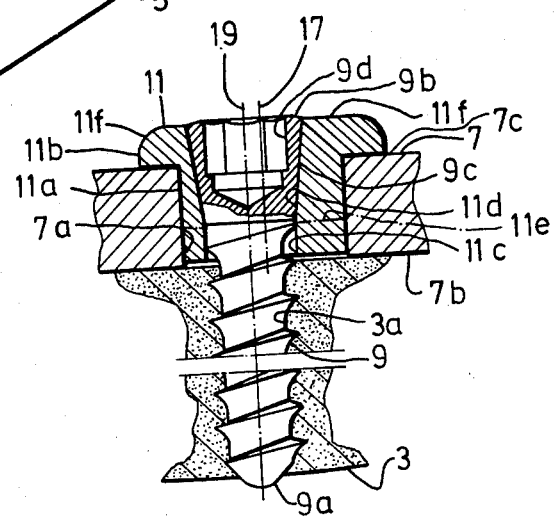
FIG. 5 shows a longitudinal section through one of the bone pieces shown in FIG. 4 and througn part of the plate fastened to the bone piece.

After setting the bone pieces straight and pushing them against one another, the plate is set into its position shown in FIG. 1 and fastened to the bone on opposite sides of the place of fracture, at first by way of its central clearance hole 7a. For this purpose, a threaded hole 3a is first drilled into the bone piece 3, as shown in FIG. 5, and the plate 7 is provisionally fastened by a screw 9 and a sleeve 11. A hole is drilled thereafter into a bone piece 5 by means of a drilling template 13 and a drill 15, the drilling template comprising a bushing insertable into the holes 7a and provided with an excentric guide bore, the drilled hole being provided thereafter with an internal thread.

As will be explained later in more detail, the two bushings 11 are so designed, that they hold the screws 9 excentrically in relation to the clearance holes 7a. As may be seen in FIGS. 1 and 2, the first two holes are drilled in such a way into the bone pieces 3 and 5 and the screws 9 and the sleeves 11 so inserted, that the screw axes first lie on that side of the corresponding clearance hole axes. which face away from the surfaces of fracture.

Each screw includes a threaded portion 9a and a head 9b. The head 9b is bounded at its periphery by a conical surface 9c, as is clearly visible in FIG. 5, which surface 9c converges from the free end of the head 9b toward the threaded portion 9a. Moreover, the head 9b is provided with an essentially hexagonal hole 9d at its outer face.

Each of the two sleeves 11 is provided with a clamping part 11a comprising a cylindrical outer surface coaxial with an axis 17 and having an outer diameter somewhat smaller than the diameter of the clearance holes 7a. Moreover, the sleeves 11 comprise a collar 11b protruding radially beyond the clamping part 11a and being made in one piece with the latter. In the mounted position of the device the collar bears against the surface of the plate facing away from the bone pieces. The clamping part is bounded by a radial surface on its side which faces toward the bone, the length dimension of the clamping part 11a being approximately equal to the thickness of the plate 7 at the thinnest place of its cross-section, so that the entire clamping part 11a can be accommodated inside a clearance hole 7a. Each sleeve 11 is also provided with an opening 11c, the axis of which is displaced in relation to the axis 17, and which evidently coincides in the mounted position of the device with the axis 19 of the screw 9 inserted into the opening 11c. The opening 11c comprises a short cylindrical section at its end facing toward the bone. In continuation of this section is another section bounded by a conical surface 11d and extending to the collar sided face of the sleeve 11. The diameter of the conical surface 11 decreases from this collar sided face toward the cylindrical section of the opening 11c, the angle enclosed by the conical surface 11d being equal to that enclosed by the conical surface 9c.

Figure 6:
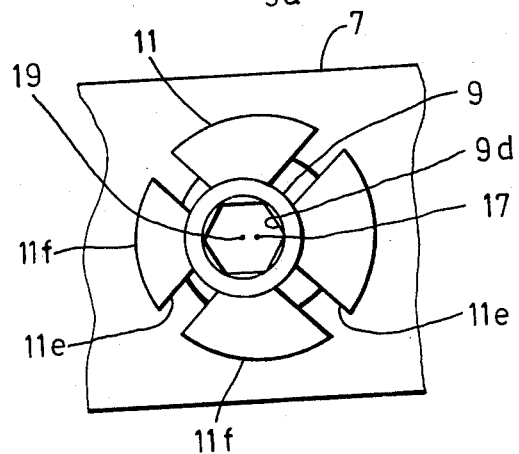
FIG. 6 shows a top view of the part of the plate shown in FIG. 5 and of a screw penetrating through it.

FIG. 6 clearly shows the sleeve 11 provided with four slots 11e bounded by planes running parallel and radially in relation to the axis 19. Moreover, the slots 11e extend from the collar sided face approximately to the thinner end of the conical surface 11d and subdivide the sleeve 11 into four tongues 11f in the region of the conical surface 11d. Because of the excentric arrangement of the opening 11c the dimensions of the four tongues vary from one another.

After inserting the sleeve 11 into the holes 7a nearest to the fracture, the screws 9 penetrating through said holes 7a are first screwed-in only to such a depth, that the sleeves may still be rotated. After that, a hollow socket wrench 21 comprising cams which fit into the slots 11e is brought in engagement with one of the sleeves 11. Moreover, a wrench 23 for socket head screws insertable into the hollow socket wrench 21 is introduced into the opening 9d of the screw 9. The sleeve 11 is then turned, as indicated by the arrow. As a result, the two bone pieces 3 and 5 are displaced in relation to each other, as indicated by the arrows 27. If a compression force pressing the bone pieces against each other is generated in this manner, the corresponding screw 9 becomes screwed tight. As a result, the screw head 9b becomes displaced in the direction of the axis 19, so that it forces the tongues 11f apart. The screw head 9b thus plays the role of an expander that pushes the tongues outwardly. This outward pressure on the tongues produces a clamping of the screw 9 in relation to the plate 7.

Since the turning of a sleeve 11 in relation to the axis 19 also causes the plate 3 to become displaced in a direction transverse to the longitudinal direction of the plate, both sleeves 11 are properly turned for spanning through about the same angle of rotation, so that the plate remains parallel to its original position.

Figure 4:
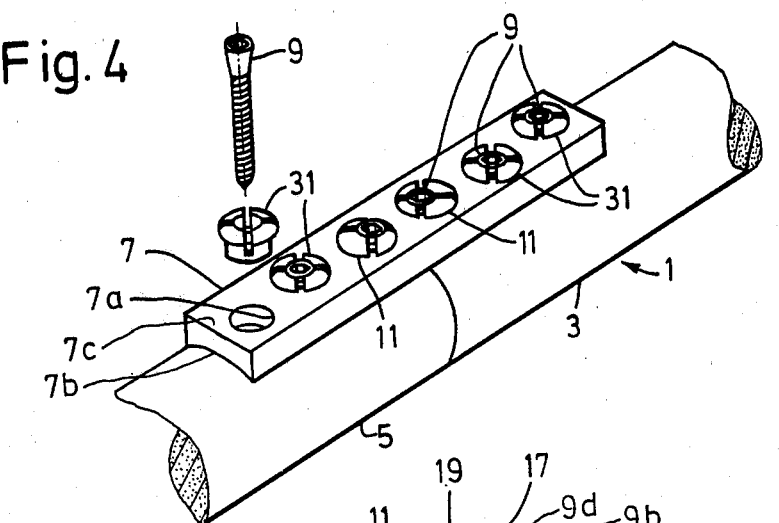
FIG. 4 shows a view of the bone pieces with plate, as shown in FIGS. 1 to 3, in a state in which the plate is almost completely screw-fastened.

Next, the bone is drilled into at the other, outer holes 7a of the plate 7. In this case, however, a drilling template having its guide bore coaxial with the holes 7a used. In addition, the sleeves 31 visible in FIG. 4 are inserted into the outer holes 7a, said sleeves 31 differing from the sleeves 11 only in that their openings are coaxial with their peripheral bounding surfaces. The sleeves 31 too, are penetrated by the screws 9 when screwed into the bone pieces. At the same time the tongues of the sleeves 31 are forced apart and the screws 9 are tightly clamped in relation to the plate 7.

The device explained by reference to FIGS. 1 to 6 has all its screws extend at right angles to the plate surface 7c which faces away from the bearing surface 7b. Thus, if the plate 7 is straight as shown in FIGS. 1 to 6, and does not have to be bent or twisted by the surgeon to make it conform to the shape of the bone, then the axes of all the screws 9 will be parallel to each other.

However, at times the surgeon may want to insert individual screws, not at right angles, but inclined in relation to the plate surface which faces away from the bearing surface of the plate. A device, which renders a screw arrangement of this kind possible is explained below with reference to FIGS. 7 to 12.

Figure 7:
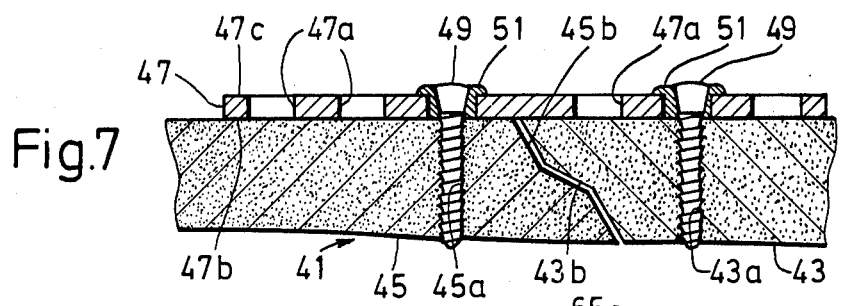
FIG. 7 shows a longitudinal section through two pieces of a bone and a plate partially fastened by two screws.

FIG. 7 shows a bone 41 broken into two pieces 43 and 45. The surfaces of fracture 43b and 45b run generally inclined in relation to the longitudinal direction of the bone. In a surgical operation the bone pieces 43 and 45 are connected with each other by means of a device comprising a plate 47. This plate 47 has a design similar to the plate 7 and comprises cylindrical clearance holes 47a distributed over its length, a bearing surface 47b in contact with the bone 41 and bent in its cross-section to fit the shape of the bone, and a plane surface 47c which faces away from the bearing surface 47b.

During the operation the plate 47 is first fastened on both sides of the fracture location by means of a screw 49 each, screwed into a threaded hole 43a and 45a, respectively, and a sleeve 51. The two screws 49 and the sleeve 51 are identical in design to the screws 9 and the sleeves 11, respectively. The process of mounting the two screws 49 takes place essentially in the manner explained with reference to the plate 7, with the difference, that the two screws 49 are inserted into clearance holes located on the two sides of a non-occupied clearance hole 47a.

Figure 8:
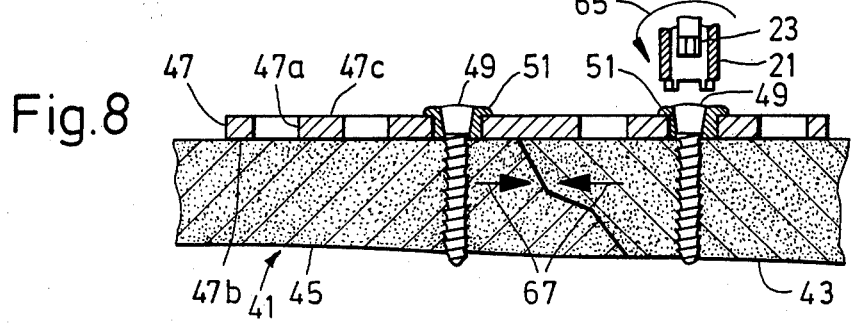
FIG. 8 shows the components of FIG. 7 with tools for pressing the bone pieces against each other.

After the two screws have been mounted, lightly at first, the two sleeves 51 are rotated one after the other by means of the aforementioned tool 21, as indicated in FIG. 8 by an arrow 65, and screwed tight by means of the wrench 23. By turning the sleeves 51 the two pieces of bone become displaced in relation to each other in the direction of the arrows 67 and pressed against each other at the surfaces of fracture. Also, the clamping parts of the sleeves 51 become tightly clamped in relation to the plate 47.

Figure 9:
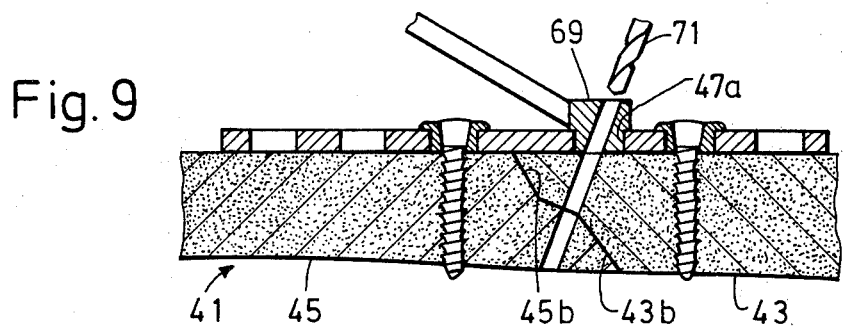
FIG. 9 shows the components of FIG. 7 with tools for drilling a hole penetrating through the surfaces of fracture of the bone pieces.

As soon as the surfaces of fracture of the two bone pieces 43 and 45 are pressed against each other, a hole is drilled in the plate 47 through the clearance hole 47a located between the two screws mounted in place, the hole being drilled, by means of a drilling template 69 and a drill 71 visible in FIG. 9, inclined in relation to the longitudinal direction of the bone 41 and made to penetrate through the surfaces of fracture 43b and 45b, so as to form in each of the two bone pieces 43 and 45 a partial hole each.

The partial hole in the bone piece 43 is then enlarged by means of a drill of larger diameter, to form a larger partial hole 43c, particularly clearly visible in FIG. 11. A thread is then cut into the partial hole of the bone piece 45, thus forming the threaded hole 45c. A sleeve 61 and a screw 59 are now inserted into the clearance hole 47a of the plate located above the inclined hole, the screw 59 being then screwed tight in place. The screw 59 is identical in design with the screws 9 and 49, except possibly for its different length dimensions, and comprises in particular a threaded portion 59a and a head 59b provided with a conical surface 59c. The sleeve 61 comprises a clamping part 61a provided with a cylindrical outer surface coaxial with the axis 55 and of nearly the same diameter as that of the clearance holes 47a. The length of the clamping part 61a is such, that the said part 61a is accommodated in its entirety within the clearance hole 47a. The sleeve 61 further comprises a collar 61b made in one piece with the clamping part 61 and disposed coaxially with the outer surface of the latter. The collar 61b protrudes radially beyond the clamping part 61a and bears against the surface 47c of the plate. The sleeve further comprises an opening 61c whose axis coincides with the axis 57 of the screw 59. The axes 55 and 57 cross one another and enclose an acute angle. The opening 61c comprises a short cylindrical section at its end adjacent to the bone 41, said section being continued by a conical surface 61d diverging toward the end of the opening which faces toward the collar. This conical surface 61d encloses a cone angle equal to the cone angle enclosed by the conical surface 59c. Four slots 61e are cut into the collar sided face of the sleeve 61 in the direction of the axis 55 and distributed over the periphery of the sleeve 61. These four slots 61e extend over a portion of the clamping part and subdivide the part of the sleeve which faces away from the bone into four tongues 61f.

Figure 10:
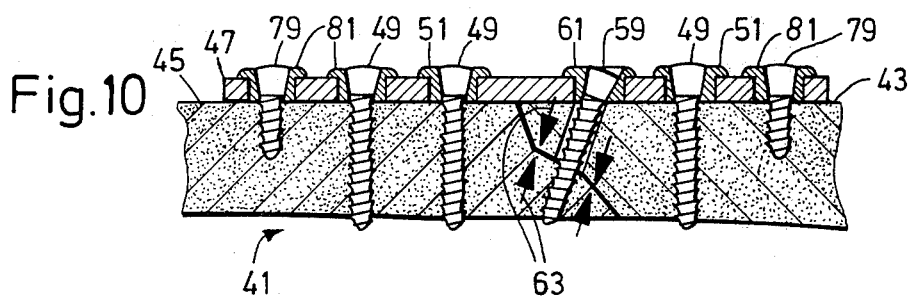
FIG. 10 shows a longitudinal section through the bone and the plate after the plate is fully clamped.

In its tightly screwed-in state, the screw 59 pulls the two pieces 43 and 45 at their surfaces of fracture 43b and 45b toward each other, by a force directed parallel to the screw axis 57, as is indicated in FIG. 10 by the arrows 63. At the same time, the conical head 59b of the screw 59 functions as an expander and forces the tongues 61f apart, so that the clamping part 61a becomes clamped within the clearance hole 47a tight in relation to the plate 47a.

Additional threaded holes may be cut into the bone 41 at the remaining three clearance holes, and sleeves inserted into the clearance holes after the screw 59 has been mounted in place. The sleeves 81 are identical in design with the sleeves 41 and, except for the slots, they are built in the shape of bodies of revolution. A screw 49 may be screwed into the plate at the clearance hole second from the left in FIG. 10, whereas shorter screws 79 may be screwed into the two outermost clearance holes, for example.

Thus, the plate 47 is fastened with screws and three different kinds of sleeves, in particular, two sleeves 51 excentric in relation to the screws, one sleeve 61 having a screw inclined in relation to the axis of the outer surface of the clamping part, and three sleeves 83 having the outer surface of the clamping part coaxial with the axis of the screw. A set of different sleeves and screws may now be made available to the surgeon, to enable him to insert one or the other kind sleeve, depending on his preference or on any particularly requirements.

Other sleeves may be made available too, having the screw axes inclined at different angles in relation to the axes of the outer surfaces of the clamping parts, to enable the surgeon to insert the screws at desired angles of tilt.

FIGS. 13 and 14 show an embodiment in which a screw may be mounted in an inclined position relativ to the plate, the angle of tilt being selected at will within certain limits.

FIG. 13 shows a portion of a bone 91 broken into two pieces 93 and 95. The two bone pieces abut against each other at the surfaces of fracture 93b and 95b. The two bone pieces 93 and 95 are joined together by way of a device comprising a plate 97 and having several clearance holes 97a distributed over the length of the plate. A hole which penetrates through the surfaces of fracture 93b and 95b is drilled in FIG. 13 into the bone 91 at the clearance hole 97a, the hole being composed of a threaded partial hole 95c drilled into the bone piece 95, and a somewhat larger, cylindrical partial hole 93c drilled into the bone piece 93.

The clearance hole 97a comprises a short cylindrical section at its end facing away from the bearing surface 97b of the plate 97. An entrance section converging toward the bearing surface and having the shape of a spherical zone extends in continuation of the cylindrical section. The end section of the clearance hole 97a which opens into the bearing surface 97b diverges toward the bearing surface 97 in the form of a conical surface.

A sleeve-shaped clamping part 101 comprising a throughgoing opening 101c is inserted into the clearance hole 97a. The opening 101c comprises a short cylindrical section at its end facing toward the bone, followed by a conical surface 101d having its diameter increasing in the direction away from the bone. The outer surface of the clamping part forms a spherical zone which extends on both sides of a plane passing through the center of the sphere. The diameter of the outer surface of the clamping part 101 is approximately equal to the diameter of the section of the clearance hole 97 shaped as a spherical zone. Four slots 101 clearly visible in FIG. 14 are cut into the end surface of the clamping part 101 which faces away from the bone, said slots 101 extending over about 80% of the height of the clamping part 101 and constituting the boundaries of the four tongues 101f.

A screw 99 comprises a threaded portion 99a passing through the partial hole 93c and screwed into the threaded hole 95c, and a head 99b comprising the clamping part 101. The clamping part 101 is outwardly bounded by a conical surface 99c which diverges in the direction away from the threaded portion 99a, and encloses a cone angle corresponding to the cone angle enclosed by the conical surface 101d. The head 99b is provided with a hexagonal hole 99d. The screw axis, which at the same time is the axis of the clamping part, is designated by the reference numeral 103.

The screw 99 and the clamping part 101 may be tilted within the clearance hole 97a in any direction, within certain limits. Thus, the axis 103 may be disposed at right angles or at a different angle in relation to the plane of the plate 97, this latter case being illustrated in FIG. 13.

The tongues 101f of the clamping part 101 are forced away from the axis 103. During this process the screw head 99b functions as an expander, which causes the clamping part 101 to become tightly clamped within the plate.

A device comprising clamping parts having their outer surfaces shaped as spherical zones, may be constructed with clamping parts having their opening for receiving the screw head disposed excentric in relation to the outer surface of said clamping part. It thus becomes possible to press the bone pieces against each other by turning the clamping parts in the manner explained with reference to FIG. 3, even if plates are used that have clearance holes with sections shaped as spherical zones.

Figure 15:
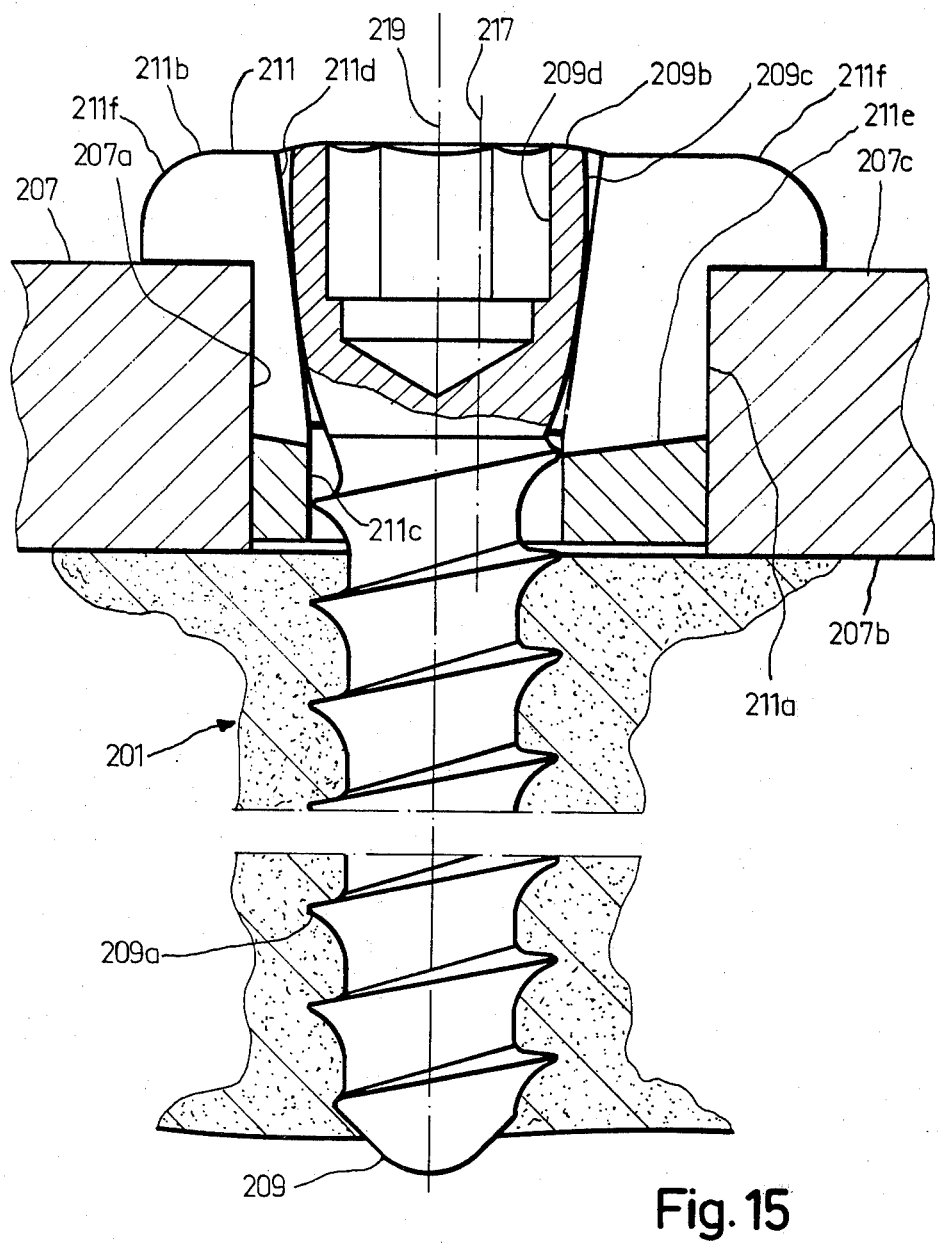
FIG. 15 shows a longitudinal section corresponding to FIG. 5 through a bone piece and through a device comprising a screw having the outer section of its head shaped convex in cross-section.

FIG. 15 shows a bone 201 having a plate 207 fastened to it for the purpose of immobilizing a fractured bone. The plate 207 comprises a number of clearance holes 207a distributed over its length, in particular cylindrical bores, and bears against the bone on a bearing surface 207 slightly concave in cross-section. The surface which faces away from the bearing surface 207b is plane.

The clamping part 211a of a sleeve 211 is inserted into the clearance hole 207a shown in FIG. 15 and representing a clearance hole located near the place of fracture. The clamping part 211a has a cylindrical outer surface coaxial with the axis 217. The sleeve 211 is provided with a collar 211b protruding axially beyond the clamping part 211a and made in one piece therewith, and bearing against the surface 207c. The sleeve 211 comprises an opening 211c, whose axis is displaced in relation to the axis 217 and coincides, in the screw position illustrated, with the axis 219 of a screw 209 penetrating through the sleeve 211. The opening 211c comprises at its end facing toward the bone a short cylindrical section continued by a section bounded by the conical surface 211d and diverging in the longitudinal direction of the axis of the opening 211c. The sleeve 114 is provided with four slots 211e, each bounded by radial and parallel surfaces in relation to the axis 219. The slots 211e extend from the face of the collar, approximately to the end having the smaller diameter of the conical surface, and subdivide the sleeve into four tongues 211f.

The screw 209 comprises a threaded portion 209a and a head 209b serving as an expander. The outer surface 209c of the head 209 is slightly convex and shaped as a spherical zone. This spherical zone is so designed, that the conical surface is engaged by the central portion of the surface 209c. In the sectional view of FIG. 15 drawn parallel to the axis 219, the tangents drawn through the points of contact of the surfaces 209c and 211d thus lie within the conical surface 211d. Moreover, the screw head comprises a blind hole 209d.

Apart from the convex design of the outer surface 209c of the screw head, the plate 207, the screw 209 and the sleeve 211 are essentially identical with the corresponding parts shown in FIGS. 5 and 6, and are mounted in an analogous manner. The convex design of the surface 209c enables the surgeon to tilt the screw 209 in relation to the axis of the opening 211c. Thus the screw 299 too, in analogy with the screws 59 and 99, may be mounted across an inclined surface of fracture.

The screw head 209b which converges in the longitudinal direction of the screw axis, at least in its lower part adjacent to the bone, thus fulfills the function of an expander forcing the clamping part 211a apart, in particular during the process of tightening the screw.

Attention is drawn to the fact, however, that the conical surface 211d could be replaced, partially or totally, by a spherical surface converging toward the bone in the longitudinal direction od the screw axis.

The components, i.e. the plates, the sleeves forming the clamping parts and the screws of the described devices, may be made of various metals or alloys or even of non-metallic materials. However, the material which the clamping parts are made of must be elastic enough, to allow the tongues to be expanded by elastic deformation.

When using one of the described devices for immobilizing and fastening the pieces of bone, the surgeon is given the possibility, to deform the longitudinally straight plates, if necessary, to make them fit the shape of the bone. In the course of the operation the screws are so tightened, that their heads and the sleeves forming the clamping parts are made to hold the plates in such a way, that the bearing surfaces of the plates bear against the bone under a certain amount of pressure. The bone pieces may also be pressed against each other in the longitudinal direction of the plate, as explained with reference to FIG. 3.

It will next be assumed, that a reabsorption of the bone material takes place around the bearing surface of the plate used. This may occur, for example, if time variable forces caused by external loads act on the bone or the bone pieces, and are large enough to more or less overcome the static compression force generated by fastening the plate, so as to result in micromovements, i.e. small relative movements between the plate and the bone pieces. This reabsorption may cause an open space to form between the bearing surface of the plate and the bone. Even if this be the case, the plate clamped tight by the expansion of the clamping parts continues to remain connected with the screws, rigidly and nondisplaceably in the axial direction. This evidently prevents the screws from loosening by themselves under the action of shocks or of other external forces.

The described devices, each comprising a plate, a number of screws and a corresponding number of sleeves, may be used to stably connect with each other the pieces of a bone, separated as a result of a fracture or by any other cause, until they grow back together into one bone. As mentioned before, the tight clamping of the screws in relation to the plate and the improvement in stability resulting therefrom, provide a guarantee, that the connection between the plate and the screws will not get loose, even if reabsorption of bone takes place. This improvement in stability acts inhibitingly on the formation and the development of bone reabsorption. The tight clamping of the screws in relation to the plate also acts against any frictional corrosion between the various components of the device.

The devices may also be modified in various ways. First, the length dimensions and the number of clearance holes provided therein may be adapted to the particular momentary requirements.

Furthermore, the width and/or height dimensions of the plates may be enlarged at the clearance holes, to make the bending resistance moment approximately constant, at least at the two clearance holes and between them, or even along the entire length of the plates. Attention is drawn in this connection to U.S. Pat. No. 4,219,015.

The plate surfaces which face away from the bone are plane in the embodiments described; however, they could be slightly bent, if necessary. Since, however, the sleeves, or at 1 least the excentric sleeves 11, 61, 211 provided with collars, must be rotable, the plates should be provided, at least in the region of the clearance holes, with ring surfaces rotationally symmetrical in relation to the axes of these holes, on which ring surfaces the sleeve collars may rest in each position of rotation.

Obviously, numerous modifications and variations of the present invention are possible in the light of the above teachings. It is therefore to be understood that within the scope of the appended claims the invention may be practiced otherwise than as specifically described herein.

I claim:

1. A device connectable with a bone, comprising a plate with at least two clearance holes; retaining means for retaining the plate on a bone and including sleeves each having a clamping part extending through the clearance hole and provided with slots and an inner contact surface and an outer surface, and a collar made of one piece with the clamping part and protruding beyond the outer surface of the latter so as to bear against the side of the plate facing away of the bone; and screws for fastening the plate to the bone and each having an axis, a threaded portion to be screwed into the bone, and an expander displaceable relative to the clamping part in an axial direction and having an outer contact surface in contact with the contact surface of the clamping part and coaxial with the screw axis in at least one position of the screw, in which position at least one of the said two contact surfaces converges in the direction of the screw axis, in such a way, that by displacing the expander, the clamping part may be clamped tight within the clearance hole.

2. A device connectable with a bone, comprising a plate with at least two clearance holes; retaining means for retaining the plate on a bone and including sleeves each having a clamping part extending through the clearance hole and provided with slots and an inner contact surface and an outer surface which bears at least in part against the surface bounding the clearance hole, the outer surface of the clamping part of at least one of said sleeves being disposed eccentric in relation to the screw axis; and screws for fastening the plate to the bone and each having an axis, a threaded portion to be screwed into the bone, and an expander displaceable relative to the clamping part in an axial direction and having a contact surface in contact with the contact surface of the clamping part and coaxial with the screw axis in at least one position of the screw, in which position at least one of the said two contact surfaces converges in the direction of the screw axis, in such a way, that by displacing the expander, the clamping part may be clamped tight within the clearance hole.

3. A device as defined in claim 2, wherein the diameter of the one converging surface decreases toward the end of the screw which faces away from the retaining means.

4. A device as defined in claim 2, wherein the expander is made in one piece with threaded portion of the screw and possesses, at least in part, a larger diameter than the threaded portion.

5. A device as defined in claim 4, wherein the clamping part comprises a section with a cylindrical outer surface, when disregarding the slots and the clearance hole is cylindrical at least in the area in clamping contact with the clamping part, the said sleeve which forms the clamping part comprising a collar made in one piece with the clamping part and protruding beyond the outer surface thereof, the collar bearing against the side of the plate which faces away from the bone.

6. A device as defined in claim 4, wherein the outer surface of the clamping part has an outer surface and the screw is mountable in a position at which the screw axis is tilted in relation to the axis of the outer surface of the clamping part.

7. A device as defined in claim 4, wherein the clamping part comprises an outer surface section, which is made in the form of a spherical surface, when disregarding the slots, and a clearance is bounded at least in part and a surface bounding the clearance hole by a surface being part of a spherical surface.

8. A device as defined in claim 4, wherein the clamping part comprises a section with a cylindrical outer surface, when disregarding the slots and the clearance hole is cylindrical at least in the area in clamping contact with the clamping part comprising a collar made in one piece with the clamping part and protruding beyond the outer surface thereof, the collar bearing against the side of the plate which faces away from the bone.

9. A device as claimed in claim 4, wherein the screw is mountable in a position at which the screw axis is tilted in relation to the axis of the outer surface of the clamping part.

10. A device as defined in claim 4, wherein the clamping part comprises an outer surface section, which is made in the form of a spherical surface, when disregarding the slots, and the clearance is bounded at least in part, by a surface being part of a spherical surface.

11. A device as defined in claim 2, wherein at least one of the clamping parts comprises an outer surface, which bears at least in part, against the surface bounding the clearance hole and disposed eccentric in relation to the screw axis.

12. A device as defined in claim 11, wherein the slots of the clamping part provided with an eccentric outer surface extend to the end surface of the clamping part which faces away from the threaded portion of the screw.

13. A device as defined in claim 2, wherein in the said position of the screw at least one section of each of the two contact surfaces of the expander and the clamping part converges in the same direction along the screw axis.

14. A device as defined in claim 12, wherein at least one of the two contact surfaces of the clamping part and the expander is a conical surface.

15. A device connectable with a bone, comprising a plate with at least two clearance holes; retaining means for retaining the plate on a bone of two bone pieces and including sleeves each having a clamping part extending through the clearance hole and provided with slots and an inner contact surface and an outer surface which bears at least in part against the surface bounding the clearance hole and the outer surface of at least one of the sleeves is disposed eccentric in relation to the screw axis, said sleeves each having a collar made of one piece with the clamping part and protruding beyond the outer surface of the latter so as to bear against the outer side of the plate facing away from the bone; and screws for fastening the plate to the bone and each having an axis, a threaded portion to be screwed into the bone, and an expander displaceable relative to the clamping part in an axial direction and having a contact surface in contact with the contact surface of the clamping part and coaxial with the screw axis in at least one position of the screw, in which position at least one of the said two contact surfaces converges in the direction of the screw axis, in such a way, that by displacing the expander, the clamping part may be clamped tight within the clearance hole, and upon rotation of said sleeve and screwing-in of said screw, the bone pieces are displaced toward and compressed to one another under the action of the eccentric outer surface of said clamping part, the screws expand the clamping part in the clearance holes of the plate, and the collars bear against the outer side of the plate.

* * * * *